US012148525B2

(12) United States Patent
Emokpae et al.

(10) Patent No.: US 12,148,525 B2
(45) Date of Patent: Nov. 19, 2024

(54) WEARABLE MULTI-MODAL SYSTEM FOR REMOTE MONITORING OF PATIENTS WITH CHRONIC OBSTRUCTIVE PULMONARY DISEASE

(71) Applicants: Lloyd E. Emokpae, Glen Burnie, MD (US); Roland N. Emokpae, Jr., Middle River, MD (US); Ulysse Worsfold, Oakland, CA (US); Wassila Lalouani, Catonsville, MD (US); Mohamed Younis, Catonsville, MD (US)

(72) Inventors: Lloyd E. Emokpae, Glen Burnie, MD (US); Roland N. Emokpae, Jr., Middle River, MD (US); Ulysse Worsfold, Oakland, CA (US); Wassila Lalouani, Catonsville, MD (US); Mohamed Younis, Catonsville, MD (US)

(73) Assignee: LASARRUS CLINIC AND RESEARCH CENTER INC., Middle River, MD (US)

( * ) Notice: Subject to any disclaimer, the term of this patent is extended or adjusted under 35 U.S.C. 154(b) by 3 days.

(21) Appl. No.: 17/897,776

(22) Filed: Aug. 29, 2022

(65) Prior Publication Data
US 2023/0074574 A1 Mar. 9, 2023

Related U.S. Application Data

(60) Provisional application No. 63/240,900, filed on Sep. 4, 2021.

(51) Int. Cl.
*G16H 50/20* (2018.01)
*G16H 40/60* (2018.01)
*A61B 5/00* (2006.01)

(52) U.S. Cl.
CPC .............. *G16H 40/60* (2018.01); *G16H 50/20* (2018.01); *A61B 5/0022* (2013.01)

(58) Field of Classification Search
CPC ....... G16H 40/60; G16H 50/20; A61B 5/0022
(Continued)

(56) References Cited

U.S. PATENT DOCUMENTS 8,340,740 B2 12/2012 Holzer et al.
8,547,982 B2 10/2013 Sultan et al.
(Continued)

FOREIGN PATENT DOCUMENTS

CN 108564942 B 9/2018
KR 20210000321 A 1/2021
RU 2752137 C1 7/2021

OTHER PUBLICATIONS

Medical Applications of Wireless Body Area Networks, Khan et al., International Journal of Digital Content Technology and its Applications, vol. 3, No. 3, Sep. 2009.
(Continued)

*Primary Examiner* — Kerri L McNally
*Assistant Examiner* — Thang D Tran
(74) *Attorney, Agent, or Firm* — U Maryland Carey School of Law (57) ABSTRACT

A system of networked sensors designed to predict the onset of chronic obstructive pulmonary disease (COPD) symptoms is disclosed. The system is worn by an individual and the sensors collect data correlated with COPD symptoms. The collected sensor data is transmitted from the device to the user's mobile device for analysis. The results of the analysis may be forwarded to a health care provider.

6 Claims, 13 Drawing Sheets

(58) Field of Classification Search
USPC .................................................. 340/539.12
See application file for complete search history.

(56) References Cited

U.S. PATENT DOCUMENTS

| | | | |
|---|---|---|---|
| 9,582,072 | B2 | 2/2017 | Connor |
| 9,687,208 | B2 | 6/2017 | Tsai et al. |
| 9,888,868 | B2 | 2/2018 | Sarrafzadeh et al. |
| 10,028,675 | B2 | 7/2018 | Patel et al. |
| 10,327,698 | B2 | 6/2019 | Biswas et al. |
| 10,456,604 | B2 | 10/2019 | Cheatham, III et al. |
| 10,542,889 | B2 | 1/2020 | Ramesh et al. |
| 10,661,010 | B1* | 5/2020 | Tsinberg ........... A61M 5/14276 |
| 10,671,838 | B1 | 6/2020 | Bogan, III et al. |
| 10,709,353 | B1* | 7/2020 | McLane .................. A61B 5/68 |
| 10,720,151 | B2 | 7/2020 | Sypniewski et al. |
| 10,765,399 | B2 | 9/2020 | Emmanouilidou et al. |
| 10,898,160 | B2* | 1/2021 | Spina ..................... A61B 7/003 |
| 10,966,681 | B2* | 4/2021 | Datta ....................... A61B 7/04 |
| 11,089,995 | B2 | 8/2021 | Mlynczak et al. |
| 11,145,400 | B1* | 10/2021 | Neumann .............. A61B 5/486 |
| 11,179,060 | B2* | 11/2021 | Odame ................. A61B 5/0823 |
| 11,272,864 | B2 | 3/2022 | Dwarika |
| 11,307,064 | B2 | 4/2022 | Choi et al. |
| 11,308,619 | B2 | 4/2022 | Sainz de Cea et al. |
| 11,484,211 | B2 | 11/2022 | Shallom |
| 2008/0281220 | A1 | 11/2008 | Sharifpour |
| 2009/0131758 | A1* | 5/2009 | Heywood .............. G16H 40/20 600/300 |
| 2011/0034818 | A1* | 2/2011 | Gat .......................... A61B 5/08 600/529 |
| 2011/0125044 | A1 | 5/2011 | Rhee et al. |
| 2012/0283598 | A1* | 11/2012 | Horii .................... A61B 5/0816 600/586 |
| 2013/0030258 | A1* | 1/2013 | Cheung .................. G16H 20/30 600/301 |
| 2014/0126732 | A1* | 5/2014 | West ...................... A61B 7/003 381/67 |
| 2015/0351690 | A1 | 12/2015 | Toth et al. |
| 2017/0071506 | A1* | 3/2017 | Dwarika ................. A61B 5/08 |
| 2017/0143977 | A1* | 5/2017 | Kaib ...................... A61N 1/046 |
| 2017/0156680 | A1* | 6/2017 | Barretto ............... A61B 5/1118 |
| 2017/0157430 | A1 | 6/2017 | Cheatham, III et al. |
| 2017/0161451 | A1 | 6/2017 | Weinstein |
| 2017/0231528 | A1* | 8/2017 | Nathan ................. A61B 5/4082 600/483 |
| 2017/0347969 | A1* | 12/2017 | Thakur ................. A61B 5/6867 |
| 2018/0035901 | A1 | 2/2018 | Cronin et al. |
| 2018/0047200 | A1* | 2/2018 | O'Hara ................. G06V 10/242 |
| 2018/0139518 | A1 | 5/2018 | Touma et al. |
| 2019/0076080 | A1* | 3/2019 | Prado ................... A61B 5/4872 |
| 2019/0088367 | A1* | 3/2019 | Stamatopoulos ...... G16H 50/20 |
| 2019/0134396 | A1 | 5/2019 | Toth et al. |
| 2019/0151640 | A1* | 5/2019 | Weber .................. A61B 5/0002 |
| 2019/0167176 | A1* | 6/2019 | Annoni ................. A61B 5/4035 |
| 2019/0167927 | A1* | 6/2019 | Dagnello ............... G06N 20/00 |
| 2019/0231262 | A1* | 8/2019 | Nasry ................... G16H 80/00 |
| 2019/0266491 | A1 | 8/2019 | Gao et al. |
| 2019/0266723 | A1* | 8/2019 | Blanchard ............ G06V 20/698 |
| 2019/0298987 | A1* | 10/2019 | Freeman ................. A61N 1/08 |
| 2019/0302460 | A1* | 10/2019 | Kaul ...................... G10L 15/00 |
| 2019/0365263 | A1* | 12/2019 | Raj ....................... A61B 5/0024 |
| 2020/0093459 | A1* | 3/2020 | Rahman .............. A61B 5/7275 |
| 2020/0183047 | A1* | 6/2020 | Denli .................... G06N 20/20 |
| 2021/0034921 | A1* | 2/2021 | Pinkovich .............. G06N 3/082 |
| 2021/0043321 | A1* | 2/2021 | Deterding .............. G16H 50/30 |
| 2021/0045656 | A1* | 2/2021 | Rahman ................ A61B 7/003 |
| 2021/0113099 | A1* | 4/2021 | Rogers ................. A61B 5/4803 |
| 2021/0128074 | A1 | 5/2021 | Leydon |
| 2021/0169326 | A1* | 6/2021 | Emokpae ............ A61B 5/0205 |
| 2021/0275023 | A1* | 9/2021 | Kalantarian ........... G16H 50/30 |
| 2021/0315480 | A1* | 10/2021 | Odame ................ A61B 5/0816 |
| 2021/0345939 | A1 | 11/2021 | Jumbe |
| 2021/0353244 | A1* | 11/2021 | Kiely ..................... A61B 6/025 |
| 2021/0369232 | A1* | 12/2021 | Chen ..................... A61B 8/085 |
| 2021/0398683 | A1* | 12/2021 | Clifford ............... A61B 5/7267 |
| 2021/0402212 | A1* | 12/2021 | Schupp ................. A61N 5/067 |
| 2022/0005601 | A1* | 1/2022 | Cox ....................... A61B 5/742 |
| 2022/0068476 | A1* | 3/2022 | Link ..................... G16H 50/20 |
| 2022/0122728 | A1* | 4/2022 | Wahl ................... A61B 5/7282 |
| 2022/0248966 | A1 | 8/2022 | Freeman et al. |
| 2022/0359070 | A1 | 11/2022 | Lalouani et al. |
| 2022/0409904 | A1* | 12/2022 | Brouns ................ A61N 1/3615 |
| 2023/0008860 | A1 | 1/2023 | Emokpae et al. |
| 2023/0177217 | A1* | 6/2023 | Hughes ................ A61B 8/4227 600/459 |
| 2023/0225695 | A1 | 7/2023 | Dodson et al. |
| 2023/0270350 | A1* | 8/2023 | Shouldice ............. G16H 40/63 600/529 |

OTHER PUBLICATIONS

Wearable and Implantable Wireless Sensor Network Solutions for Healthcare Monitoring, Darwish et al., Sensors, 2011, vol. 11, pp. 5561-5595; May 26, 2011.
Benchmarking of eight recurrent neural network variants for breath phase and adventitious sound detection on a self-developed open-access lung sound database—HF_Lung_V1, Hsu et al., 2021 https://arxiv.org/pdf/2102.03049.pdf.
Multi-channel lung sound classification with convolutional recurrent neural networks, Messner et al., Computers in Biology and Medicine, vol. 122, 2020, 103831, ISSN 0010-4825 https://www.sciencedirect.com/science/article/abs/pii/S0010482520301955?via%3Dihub.
Investigating into segmentation methods for diagnosis of respiratory diseases using adventitious respiratory sounds, Wu et al., 42nd Annual International Conference of the IEEE Engineering in Medicine Biology Society, 2020, https://kar.kent.ac.uk/83024/1/09175783.pdf.
Deep learning based respiratory sound analysis for detection of chronic obstructive pulmonary disease, Srivastava et al., PeerJ Computer Science 7:e369 https://peerj.com/articles/cs-369/.
Altan, G., Kutlu, Y., & Allahverdi, N. (2019). Deep learning on computerized analysis of chronic obstructive pulmonary disease. IEEE journal of biomedical and health informative, 24(5), 1344-1350.
Bhalla, S., Liaqat, S., Wu, R., Gershon, A. S., de Lara, E., & Mariakakis, A. (2023). PulmoListener: Continuous Acoustic Monitoring of Chronic Obstructive Pulmonary Disease in the Wild. Proceedings of the ACM on the Interactive, Mobile, Wearable and Ubiquitous Technologies, 7(3), 1-24.
Emokpae, L. E., Emokpae Jr, R. N., Bowry, E., Bin Saif, J., Mahmud, M., Lalouani, W., . . . & Joyner Jr, R. L. (2022). A wearable multi-modal acoustic system for breathing analysis. The Journal of the Acoustical Society of America, 151(2), 1033-1038.
Fernandez-Granero, M. A., Sanchez-Morillo, D., & Leon-Jimenez, A. (2015). Computerised analysis of telemonitored respiratory sounds for predicting acute exacerbations of COPD. Sensors, 15(10), 26978-26996.
Frerichs, I., Paradiso, R., Kilintzis, V., Rocha, B. M., Braun, F., Rapin, M., . . . & Wacker, J. (2023). Wearable pulmonary monitoring system with integrated functional lung imaging and chest sound recording: a clinical investigation in healthy subjects. Physiological Measurement, 44(4), 045002.
Hawthorne, G., Greening, N., Esliger, D., Briggs-Price, S., Richardson, M., Chaplin, E., . . . & Orme, M. W. (2022). Usability of wearable multiparameter technology to continuously monitor free-living vital signs in people living with chronic obstructive pulmonary disease: prospective observational study. JMIR Human Factors, 9(1), e30091.
Islam, B., Rahman, M. M., Ahmed, T., Ahmed, M. Y., Hasan, M. M., Nathan, V., . . . & Gao, J. A. (2021). BreathTrack: detecting regular breathing phases from unannotated acoustic data captured by a smartphone. Proceeding of the ACM on Interactive, Mobile, Wearable and Ubiquitous Technologies, 5(3), 1-22.
Kaul S. Remap-West-Flare—FLAg for Review Efficacy Investigation REMAPWESTFLARE). Feb. 2023. Report No. NCT05745155.

(56) References Cited

OTHER PUBLICATIONS

Kumar, A., Mitra, V., Oliver, C., Ullal, A., Biddulph, M., & Mance, I. (Nov. 2021). Estimating respiratory rate from breath audio obtained through wearable microphones. In 2021 43rd Annual International Conference of the IEEE Engineering in Medicine & Biology Society (EMBC) (pp. 7310-7315). IEEE.

Lalouani, W., Younis, M., Emokpae Jr, R. N., & Emokpae, L.E. (2022). Enabling effective breathing sound analysis for automated diagnosis of lung diseases. Smart Health, 26, 100329.

Larson, E. C., Goel, M., Boriello, G., Heltshe, S., Rosenfeld, M., & Patel, S. N. (Sep. 2012). SpiroSmart: using a microphone to measure lung function on a mobile phone. In Proceedings fo the 2012 ACM Conference on ubiquitous computing (pp. 280-289).

Lee, S. H., Kim, Y.S., Yeo, M. K., Mahmood, M., Zavanelli, N., Chung, C., . . . & Yeo, W. H. (2022). Fully portable continuous real-time auscultation with a soft wearable stethoscope designed for automated disease diagnosis. Science Advances, 8(21), eabo5867.

Lewandowski, M., Placzek, B., & Bernas, M. (2020). Classifier-based data transmission reduction in wearable sensor network for human activity monitoring. Sensors, 21(1), 85.

Liao, X., Wu, Y., Jiang, N., Sun, J., Xu, W., Gao, S., . . . & Li, Q. (2023). Automated detection of abnormal respiratory sound from electronic stethoscope and mobile phone using MobileNetV2. Biocybernetics and Biomedical Engineering, 43(4), 763-775.

Rahman, M. M., Ahmed, T., Nemati, E., Nathan, V., Vatanparvar, K., Blackstock, E., & Kuang, J. (Mar. 2020). Exhalesense: Detecting high fidelity forced exhalations to estimate lung obstruction on smartphones. In 2020 IEEE International Conference on Pervasive Computing and Communications (PerCom) (pp. 1-10). IEEE.

Tayeh, G. B., Makhoul, A., Laiymani, D., & Demerjian, J. (2018). A distributed real-time data prediction and adaptive sensing approach for wireless sensor networks. Pervasive and Mobile Computing, 49, 62-75.

Viswanath, V., Garrison, J., & Patel, S. (Jul. 2018). SpiroConfidence: determining the validity of smartphone based spirometry using machine learning. In 2018 40th Annual International Conference of the IEEE Engineering in Medicine and Biology Society (EMBC) (pp. 5499-5502). IEEE.

Vito, D. (2012). A new system for tailoring and monitoring mechanical ventilation by a wearable device at home, Chapter 3, "Materials and Methods." Downloaded Jun. 10, 2024 from https://www.politesi.polimi.it/bitstream/10589/65161/5/2012_10_Vito.pdf.

Xie, W., Hu, Q., Zhang, Q. (2023). EarSpiro: Earphone-based Spirometry for Lung Function Assessment. Proceedings of the ACM on Interactive, Mobile, Wearable and Ubiquitous Technologies, 6(4), 1-27.

Xu, W., Huang M. C., Liu, J. J., Ren, F., Shen, X., & Sarrafzadeh, M. (May 2013). MCOPD: mobile phone based lung function diagnosis and exercise system for COPD. In Proceeding of the 6th International Conference on PErvasive Technologies Related to Assistive Environments (pp. 1-8).

Zubaydi, F., Sagahyroon, A., Aloul, F., Mir, H., & Mahboub, B. (Dec. 2020). Using mobiles to monitor respiratory diseases. In Informatics (vol. 7, No. 4, p. 56). MDPI.

Majumder AK. Computer Analysis of Frequency Spectrum of the Phonopulmogram. Proc Annu Symp Comput Appl Med Care. Nov. 5, 1980; 1 :266-71. PMCID: PMC2203739.

Kemalasari et al., Medical Spirometer for Diagnosing COPD Base On The Measurement of FVC and FEV1, 2020 J. Phys.: Conf. Ser. 1569 032061.

\* cited by examiner

WEARABLE MULTI-MODAL SYSTEM FOR REMOTE MONITORING OF PATIENTS WITH CHRONIC OBSTRUCTIVE PULMONARY DISEASE

CROSS REFERENCE TO RELATED APPLICATIONS

This application claims the benefit of U.S. Provisional Application Ser. No. 63/240,900, filed Sep. 4, 2021, the disclosure of which is incorporated by reference in its entirety.

BACKGROUND OF THE INVENTION

Chronic Obstructive Pulmonary Disease (COPD) can lead to the hospitalization of patients afflicted by the disease. Improving the ability to monitor patients afflicted by or potentially afflicted by COPD would be beneficial.

BRIEF SUMMARY OF THE INVENTION

This invention relates to a system used to predict the onset of COPD systems. A system is worn which contains a plurality of sensors. The data produced by the sensors are fed into a machine learning system which predicts whether or not the user is likely to experience COPD symptoms. The output of the prediction can be used for further analysis.

Further embodiments, features, and advantages of the present invention, as well as the operation of the various embodiments of the present invention, are described below with reference to the accompanying drawings.

DETAILED DESCRIPTION OF THE INVENTION

A preferred embodiment of the present invention is now described with reference to the figures, where like reference numbers indicate identical or functionally similar elements. Also in the figures, the leftmost digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other systems and applications.

Figure 1:
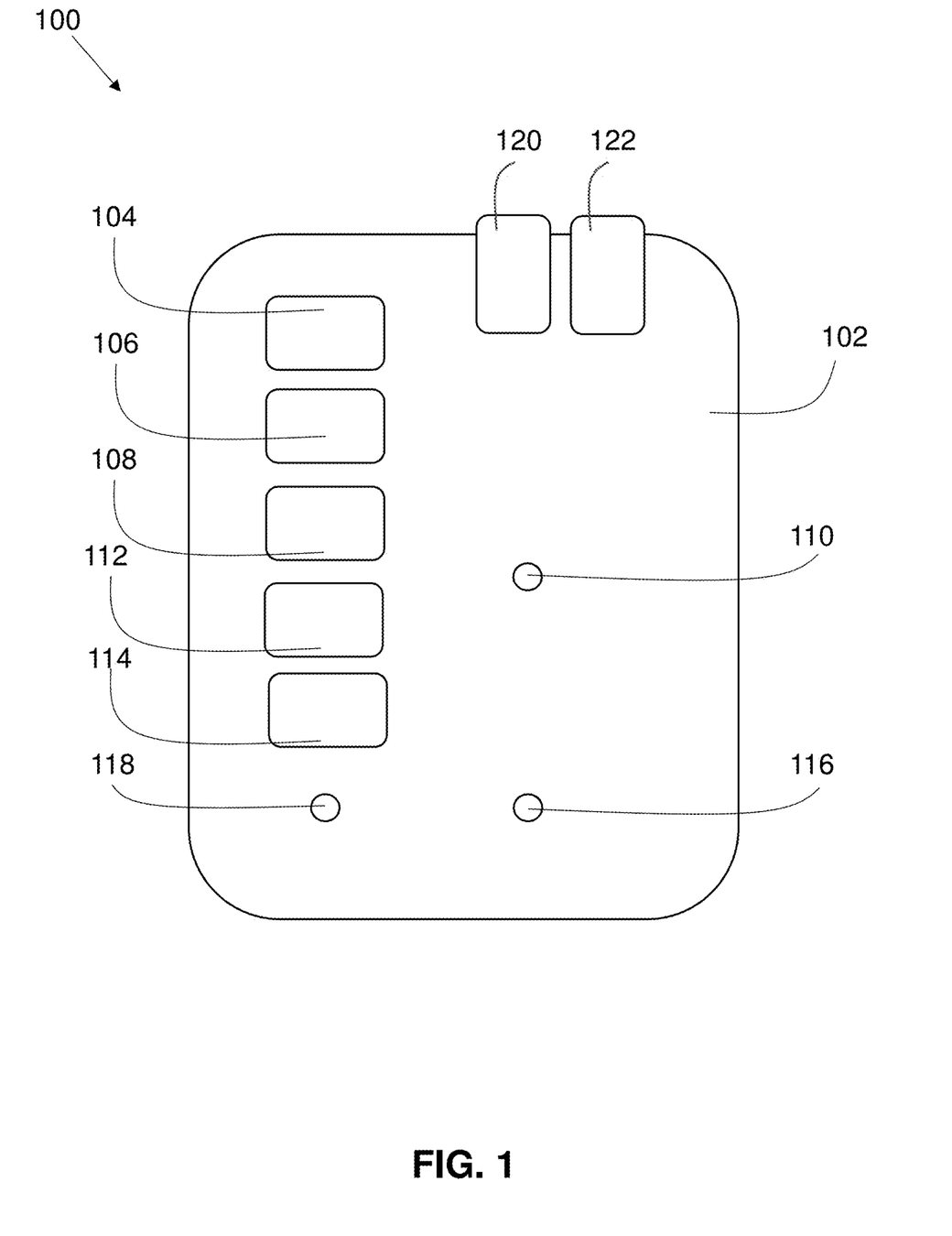
FIG. 1 shows a cutout view of a wearable sensor according to an embodiment.

Referring to FIG. 1, a system 100 may be used to aid patients afflicted by COPD. COPD is a chronic inflammatory lung disease causing airflow to and from the lungs to be obstructed. During the course of the disease, affected individuals can experience exacerbated symptoms that may lead to hospitalization.

Symptoms associated with COPD include dyspnea, coughing, and the production of sputum. While most of these symptoms can be treated in a home setting, early detection and monitoring is important to reduce the chance of hospitalization. Allowing individuals to become aware of future symptomatic events will help reduce hospital admissions and reduce costs associated with healthcare. The system 100 can aid in the prediction of exacerbated COPD symptoms.

The system 100 may contain a first housing 102. The first housing 102 provides support for the bottom of the system 100. The first housing 102 may be made of medical grade plastic (e.g., PETG). In another embodiment, first housing 102 may be made of a different waterproof material. The first housing 102 may be formed in a rectangular shape. In another embodiment, the shape of the first housing 102 may changed based on the application.

The sensor may also contain a rechargeable battery 104. The battery 104 may be any type suitable for the application (e.g., lithium, alkaline). The battery 104 may be attached to the first housing 102 by any means to prevent movement of the battery 104. The battery 104 may be capable of outputting electricity sufficient to power multiple electrical devices. The battery 104 may be rechargeable and/or replaceable.

The system 100 may also contain a radio 106. The radio 106 may be in electrical connection with the battery 104 to receive power. The radio 106 may be capable of transmitting and receiving on various radio frequencies.

The system 100 may also contain a digital microphone array 108. The digital microphone array 108 may be in electrical connection with the battery 104. The digital microphone array 108 may contain one or more microphones capable of capturing auditory signals from the environment. The digital microphone array 108 may also be in electrical connection with the radio 106.

The system 100 may also contain a digital stethoscope 110. The digital stethoscope 110 may be in electrical communication with the battery 104. The digital stethoscope may be capable of performing auscultation on the user wearing the system 100. The digital stethoscope 110 may also be in electrical connection with the radio 106.

The system 100 may also contain a thermometer 112. The thermometer 112 may be in electrical connection with the battery 104. The thermometer 112 may be capable of sensing the body temperature of the user wearing the system 100. The thermometer 112 may also be in electrical connection with the radio 106.

The system 100 may also contain a goniometer 114. The goniometer 114 may be in electrical connection with the battery 104. The goniometer 114 may be capable of sensing changes in physical orientation and serve as a body posture tracker.

The system 100 may contain one or more light emitting diode (LED) lights 116. The LED lights 116 may be in electrical connection with the battery 104. Tire LED lights may be capable of displaying different colors. Each color may correspond to a different status or state of the system 100. For example, the light 116 may be green if the system 100 is functioning properly. A red light may be shown if the battery 104 is almost out of power or a component of the system 100 is malfunctioning.

The system 100 may contain a switch 118 to actuate the power of the sensor. The switch 118 may be in electrical connection with the battery 104. The switch 118 may have an ON position, and an OFF position. When moved into the ON position, tire switch 118 may signal the battery 104 to provide power to the system 100. When moved into the OFF position, the switch may signal the battery 104 to cease providing power to the system 100.

The system 100 may contain a first port 120. The first port 120 may be configured to meet the universal serial bus standard. This may be beneficial so that the user can connect peripheral devices to the system 100. The first port 120 may be in electrical connection with the battery 104. The first port 120 may enable the battery 104 to be charged.

The system 100 may contain a second port 122. The second port 122 may be configured to connect to an electrocardiogram device. The electrocardiogram may be capable of measuring a human heart's electrical activity. The second port 122 may allow the electrocardiogram to be in electrical connection with the battery 104 and the radio 106.

Figure 2:
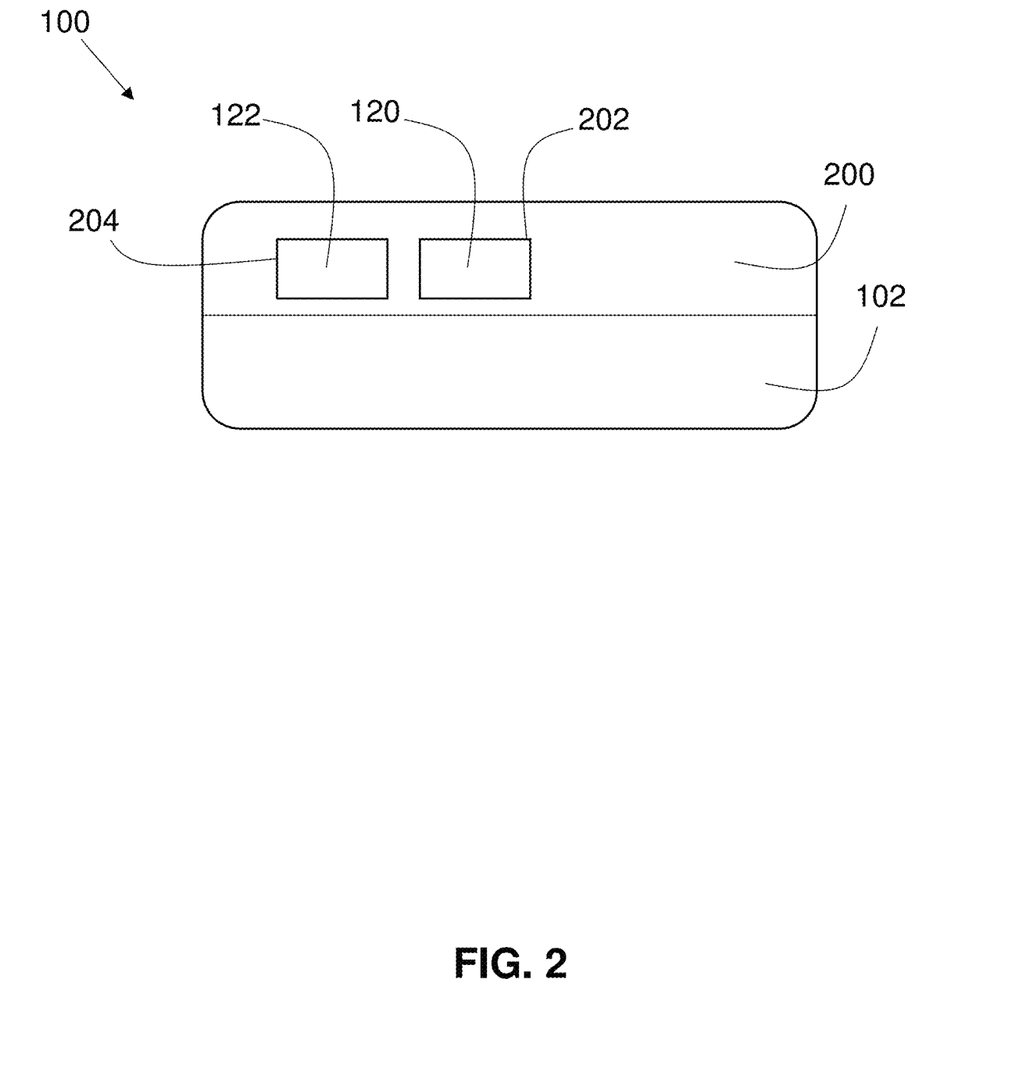
FIG. 2 shows a head-on view of the sensor of FIG. 1.

Referring to FIG. 2, the system 100 may also have a second housing 200. The second housing 200 may be made of medical grade plastic (e.g., PETG). In another embodiment, second housing 200 may be made of a different waterproof material. The second housing 200 may join with the first housing 102 to form a seal therebetween, where the housings collectively form an interior cavity in which the components of FIG. 1 are affixed. The second housing 200 and first housing 102 may be sealed by any suitable connector type (e.g., latch, hinge). The connection between the first housing 102 and the second housing 200 may be watertight so as to protect the sensors within the enclosure formed by the connection. The dimensions of the second housing 200 may match the dimensions of the first housing 102.

The second housing 200 may contain a first cutout 202. The first cutout 202 may provide access to the first port 120. This will allow the user to access the first port 120 without having to remove or disconnect either the first housing 102 or the second housing 200. The first cutout 202 may have a seal between it and the first port 120. The seal may be watertight.

The second housing 200 may contain a second cutout 204. The second cutout 204 may provide access to the second port 122. This will allow the user to access the second port 122 without having to remove or disconnect either the first housing 102 or the second housing 200. The second cutout 204 may have a seal between it and the second port 122. The seal may be watertight.

Figure 3:
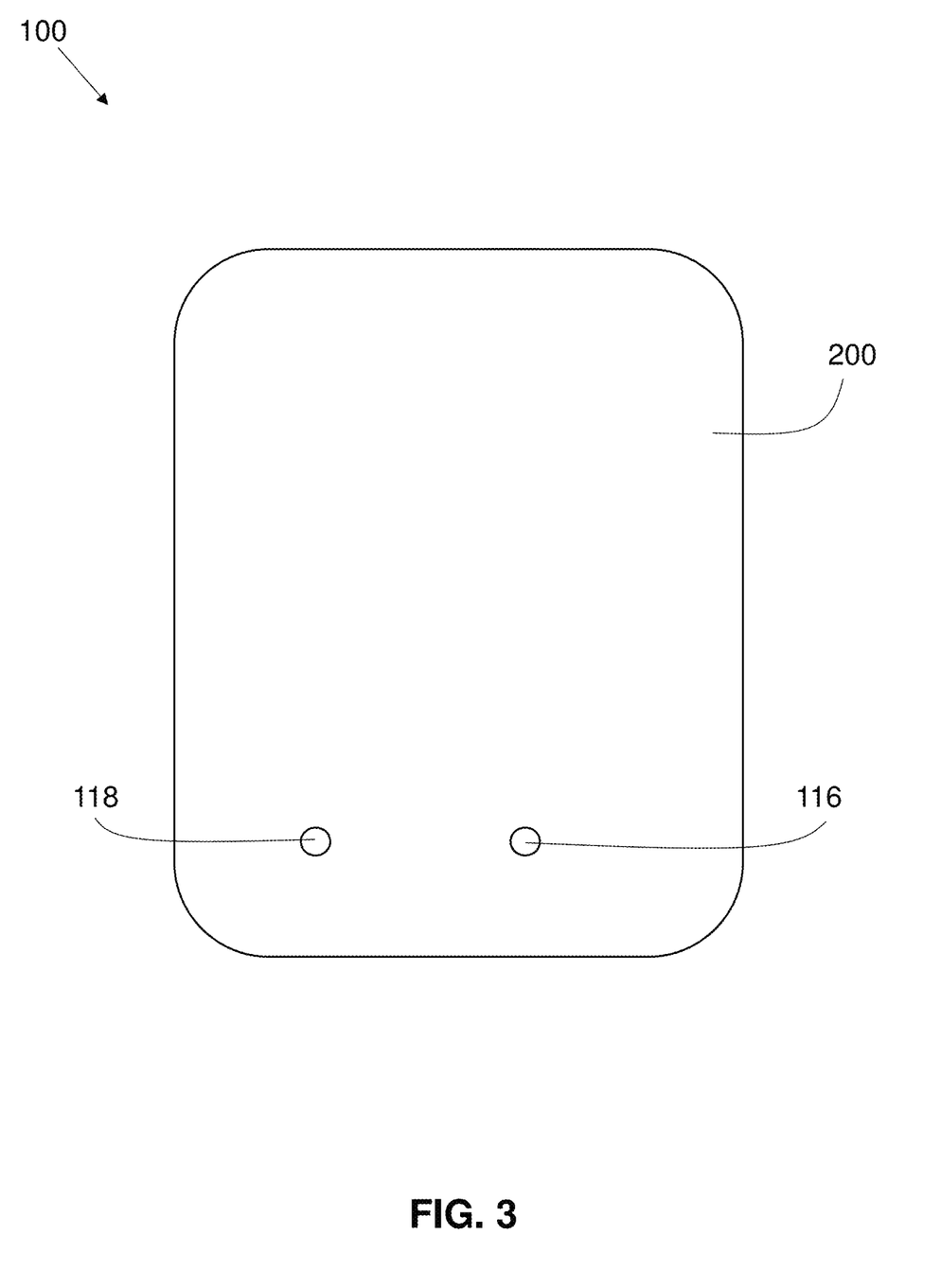
FIG. 3 shows the sensor of FIG. 1 that is sealed according to an embodiment.

Referring to FIG. 3, a top down view is shown of the system 100 with the second housing 200 in place. While in this orientation, the LED lights 116 may be visible. There may be a seal placed between the LED lights 116 and the second housing 200. This seal may be watertight. The switch 118 may be accessible from the exterior of the second housing 200. This may be desirable so that the user can activate the system 100 without having to remove either the first housing 102 or the second housing 200.

Figure 4:
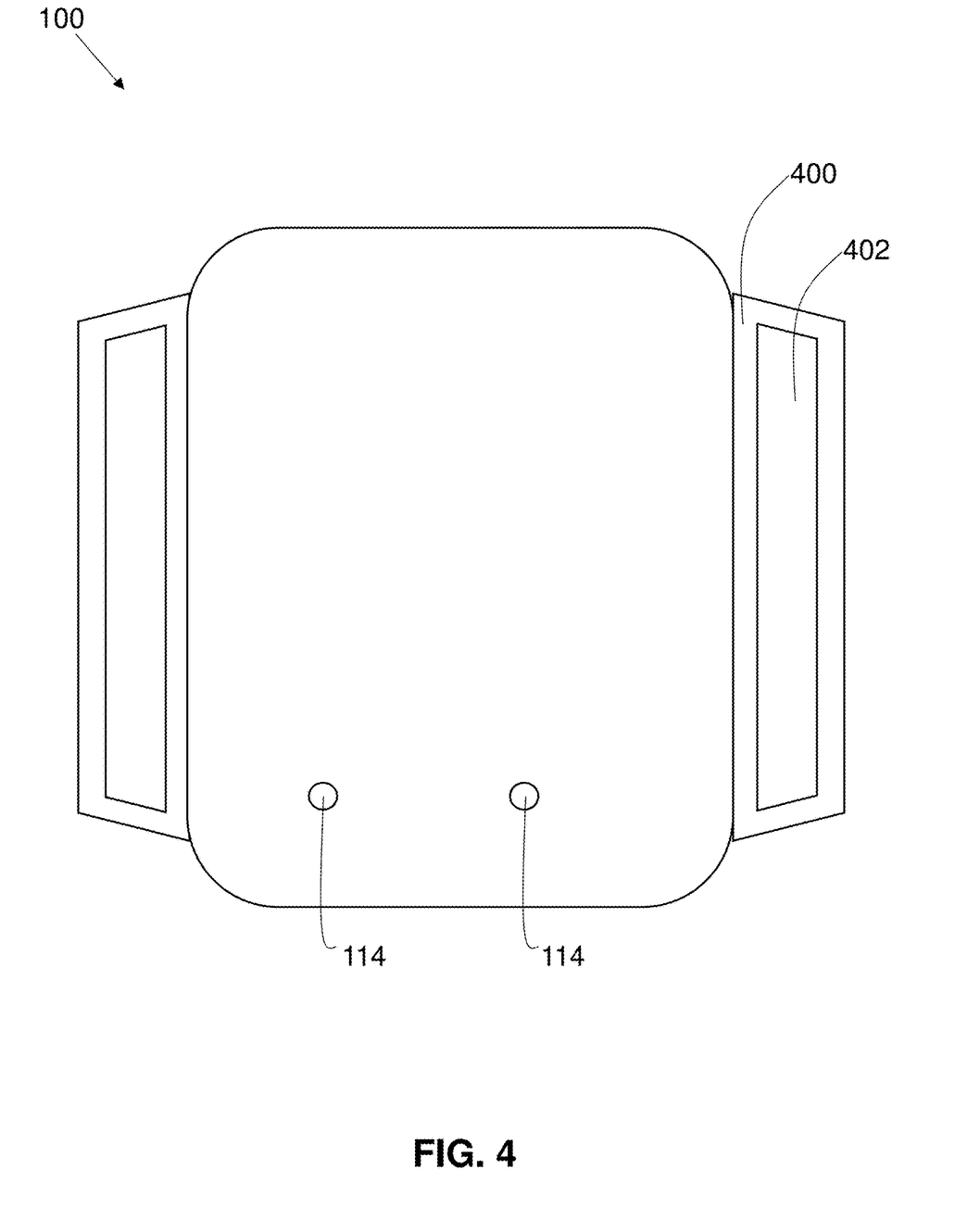
FIG. 4 shows the sensor of FIG. 1 with strap attachment points according to an embodiment.

Referring to FIG. 4, the system 100 may be configured with a pair of attachment points 400. Each attachment point 400 may contain a gap 402. The gap 402 allows for a strap to pass through one gap 400, around the system 100, and through the second gap 400. This configuration allows the user to use the sensor while it is strapped to their body. Each attachment point 400 may be made of medical grade plastic or other suitable material. Each attachment point 400 may be connected to the system 100 by any suitable means (e.g., screws, glue). The strap may be provided to the user with the system 100 or may be purchased after the fact.

Figure 5:
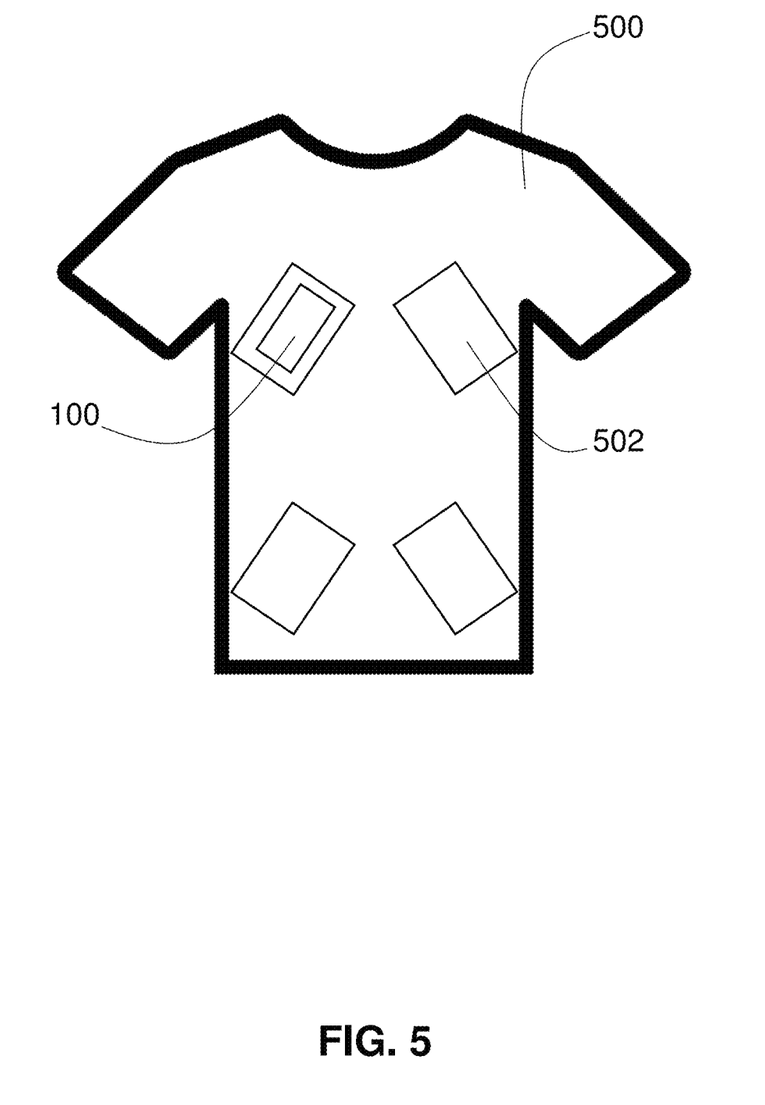
FIG. 5 shows the sensor of FIG. 1 positioned within a shirt according to an embodiment.

Referring to FIG. 5, a shirt 500 is shown. The shirt 500 may contain one or more pockets 502. Each pocket 502 may be large enough to store the system 100. The pockets 502 may be located on the exterior or interior of the shirt 500. The pockets 502 may be sewn into the shirt 500 at the time of manufacture. In another embodiment, the pockets 502 may be added after the shirt 500 has been manufactured. This embodiment would allow the user to place the system 100 within a pocket 502 as a method to carry the system 100.

Various applications may require the simultaneous use of two or more of the systems. In such a case, the set of systems represents a body area sensor network with each node (e.g., each instantiation of system 100) having a suite of sensors (e.g., digital stethoscope (microphone array) for auscultation, ECG monitor, temperature sensor and body posture tracker). Note that the use of a digital stethoscope in each of several nodes allows for listening to both lungs simultaneously to better correlate the source of exacerbation (left or right lung). Moreover the information from the multiple ECG sensors can be used to analyze lung sounds while removing any unwanted heart sounds during breathing analysis.

One of the systems 100 may serve as a gateway node that receives data collected by the other systems 100 and outputs the aggregated data for further processing at a computing device running a software application. This computing device may the user's mobile device and/or a remote computing system acting as a server.

Figure 6:
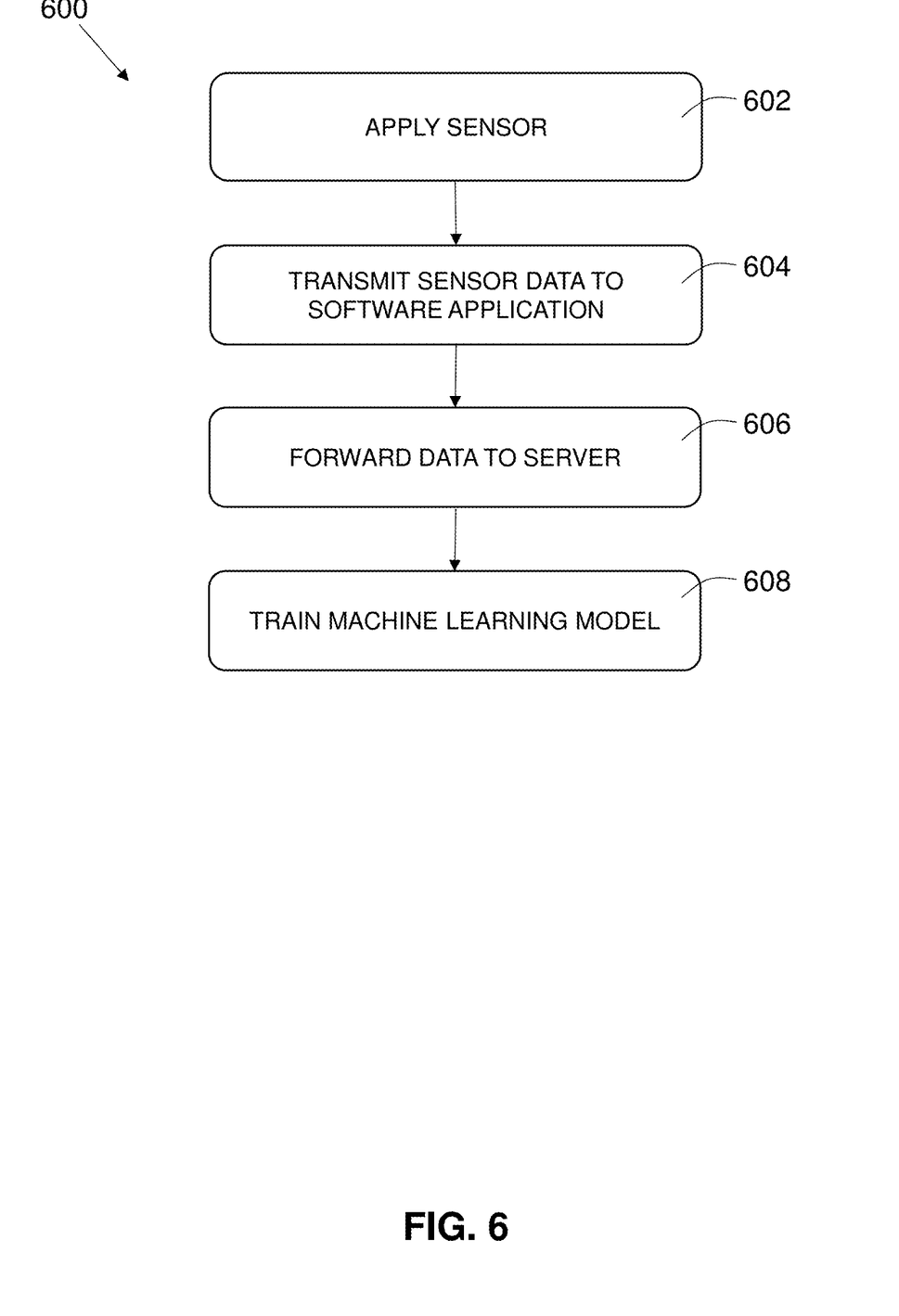
FIG. 6 shows the steps of using the sensor of FIG. 1 according to an embodiment.

Referring to the flowchart of FIG. 6, the user may apply the system 100 according to the indicated process 600. At 602 the user may apply the sensor by connecting the system 100 via straps to their body. In another embodiment, the system 100 may be placed in a shirt pocket. Alternative means for attachment may also be used. The system 100 may be activated and begin gathering sensor data. At 604, the collected data may be transmitted to a software application via the radio 106. The software application may be installed on the user's mobile device (e.g., cell phone) or other connected computing device. Upon receiving the data, the software application may then transmit the received data to a server at 606. The server may share the same computing platform as the software application. In another embodiment, the server may be located at a different device than where the software application is installed. Once received by the server, the data may be used to train a machine learning model at 608.

Figure 7:
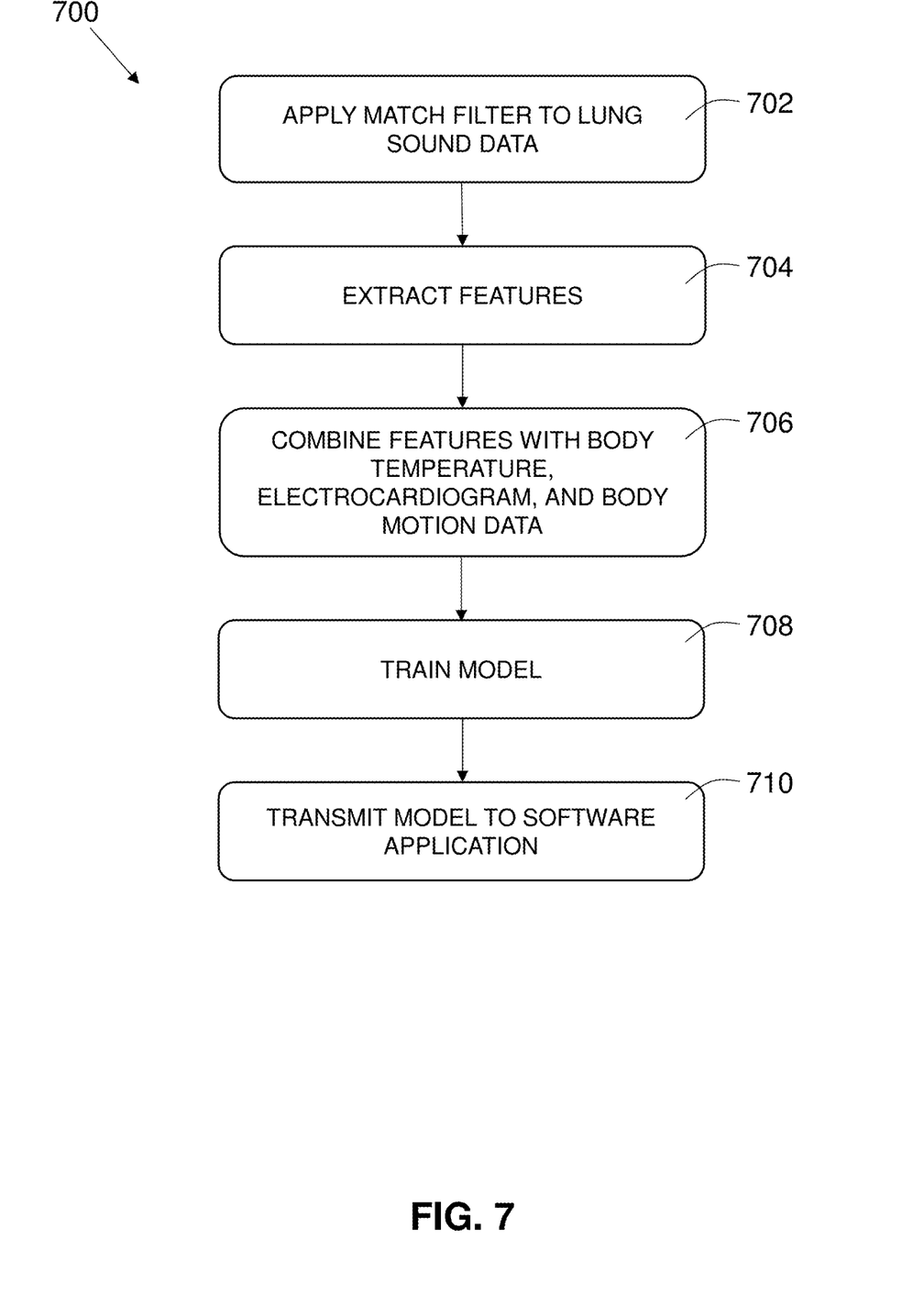
FIG. 7 shows the steps of training a machine learning model on data from the sensor of FIG. 1 according to an embodiment.

Referring to FIG. 7, the steps of training the machine learning mode are disclosed according to an embodiment. The model may be constructed as a long short-term memory model. The benefit of using this architecture is that the model is sensitive to the temporal nature of the data it is trained on. The training process may begin at 702 by applying a match filter to the data associated with the patient's lung sounds. Next, features may be extracted from the data at 704. The extracted features may be combined with other sensor data at 706. The other sensor data may be comprised of the user's body temperature, electrocardiogram data, and body motion data, for example. Next, the machine learning model may be trained at 708. The model may use the above data in the training process. Once the training process terminates, the model may be transmitted to the software application 710. The software application may execute on the user's mobile device and/or other connected computing device.

Figure 8:
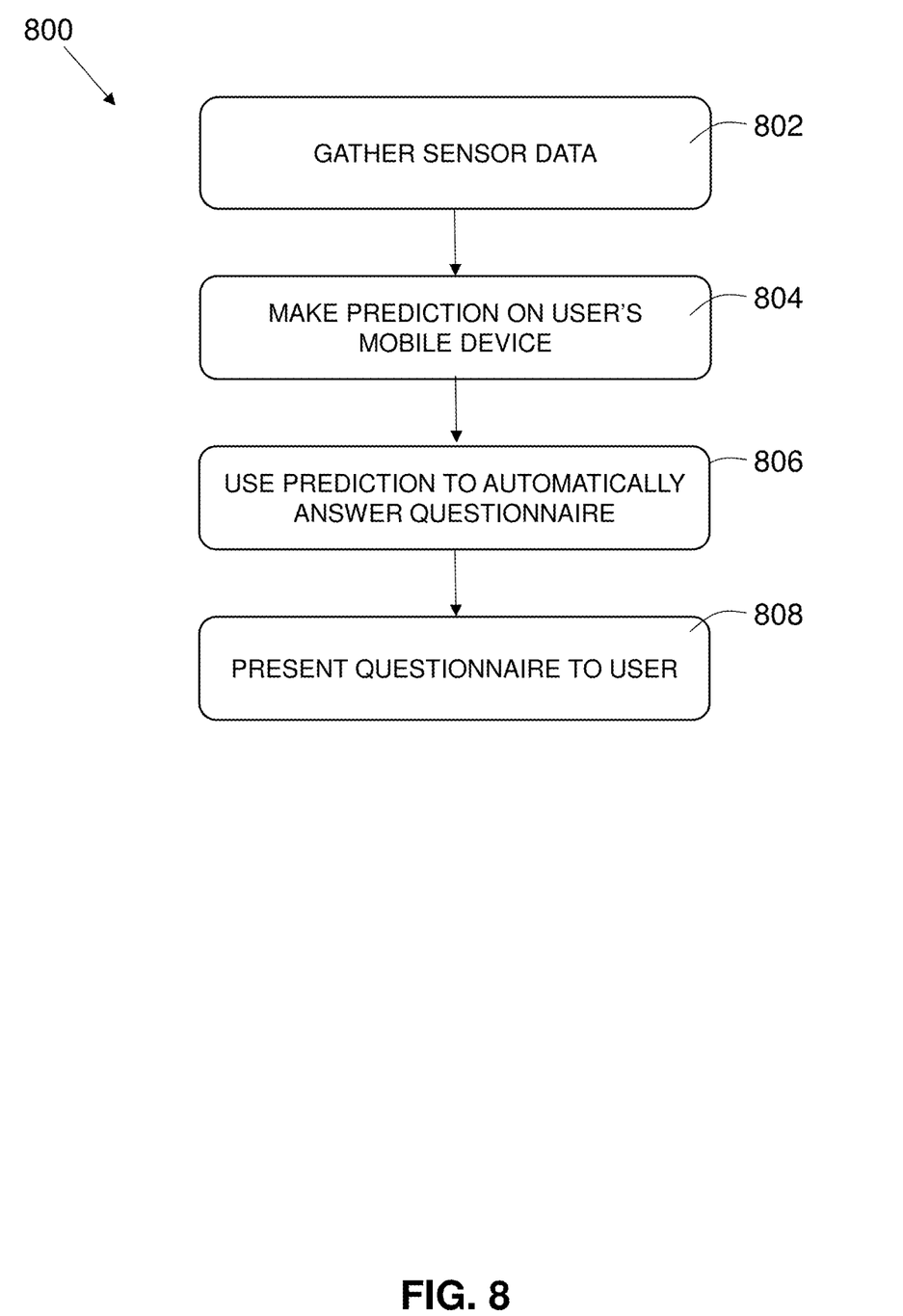
FIG. 8 shows how the output of FIG. 7 may be used to answer a patient questionnaire according to an embodiment.

Referring to FIG. 8, a process for utilizing the trained machine learning model is disclosed. At 802 the system 100 may gather data from the sensors contained within it. The data may be gathered at a gateway node. The data collected may then be analyzed by the machine learning model and a prediction generated at 804. The prediction may relate to the severity of the user's COPD symptoms. At 806 the prediction may then be used to automatically answer a questionnaire associated with COPD symptoms. The questionnaire may be within the software application running on the user's mobile device or other computing device. The questionnaire may be presented to the user at 808; the user may be able to view the questionnaire and edit the responses. The user may interact with the software application via a customizable user avatar. The avatar may act as a wearable assistant and help the user interpret the data generated by the system 100.

Figure 9:
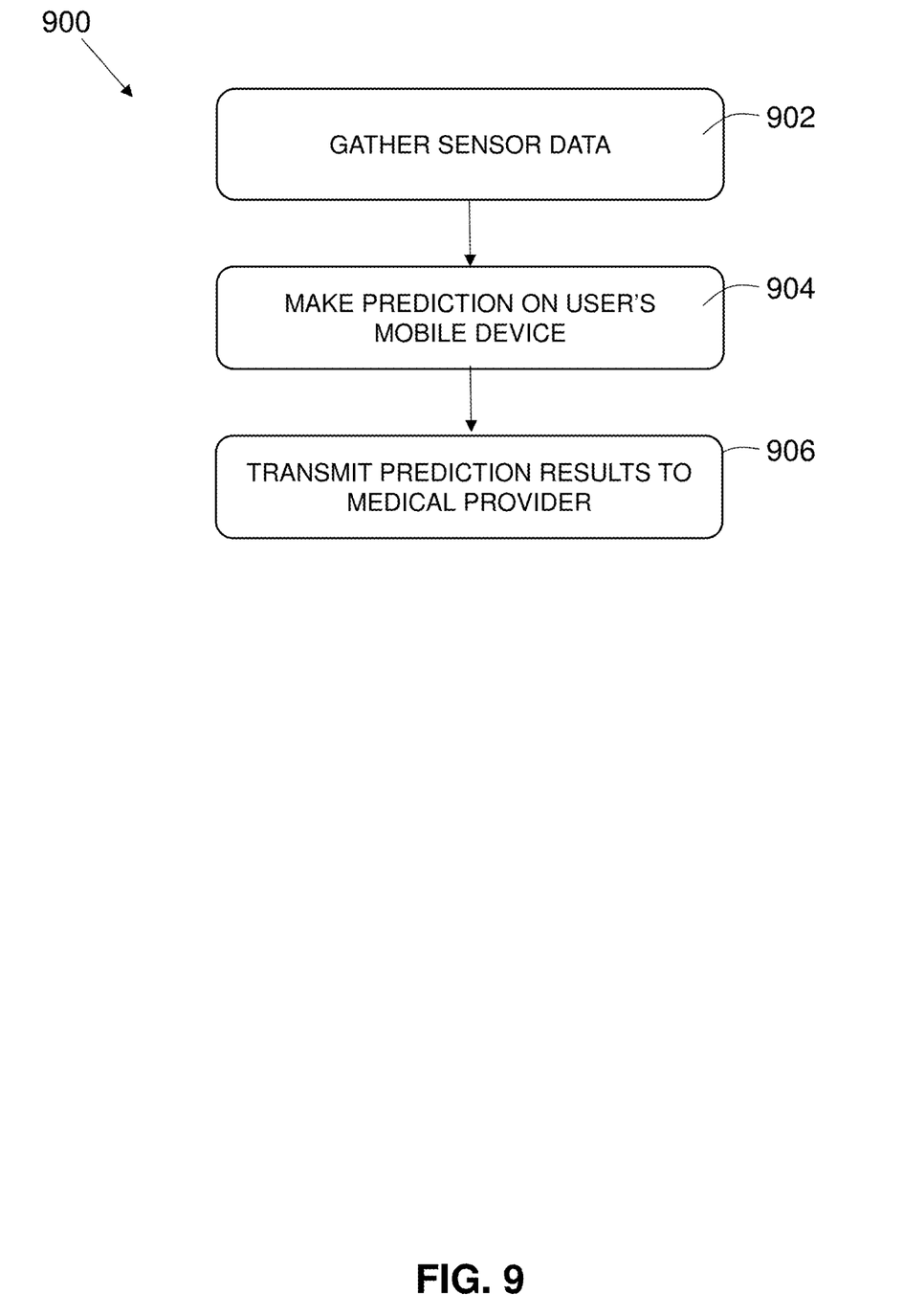
FIG. 9 shows how the output of FIG. 7 may be transmitted to a medical provider.

Referring to method 900 illustrated in FIG. 9, following GATHER SENSOR DATA step 902 and MAKE PREDICTION ON USER'S MOBILE DEVICE step 904, the prediction generated regarding the user's COPD symptoms may also be forwarded to a medical provider (906). It may be beneficial to alert the user's medical provider that the user is experiencing or about to experience a medical emergency. This will allow the medical provider to step in and prevent the user's symptoms from worsening. This will in turn prevent the user from having to go to the hospital.

The prediction may be transmitted in a format that is accepted by the medical provider. In one embodiment, the data may be formatted according to the Fast Healthcare Interoperability Resource standard. This standard allows communication with electronic medical records and electronic health records frequently used by physicians and hospitals. The software application may be capable of packaging the data to comply with the Fast Healthcare Interoperability Resource format.

Figure 10:
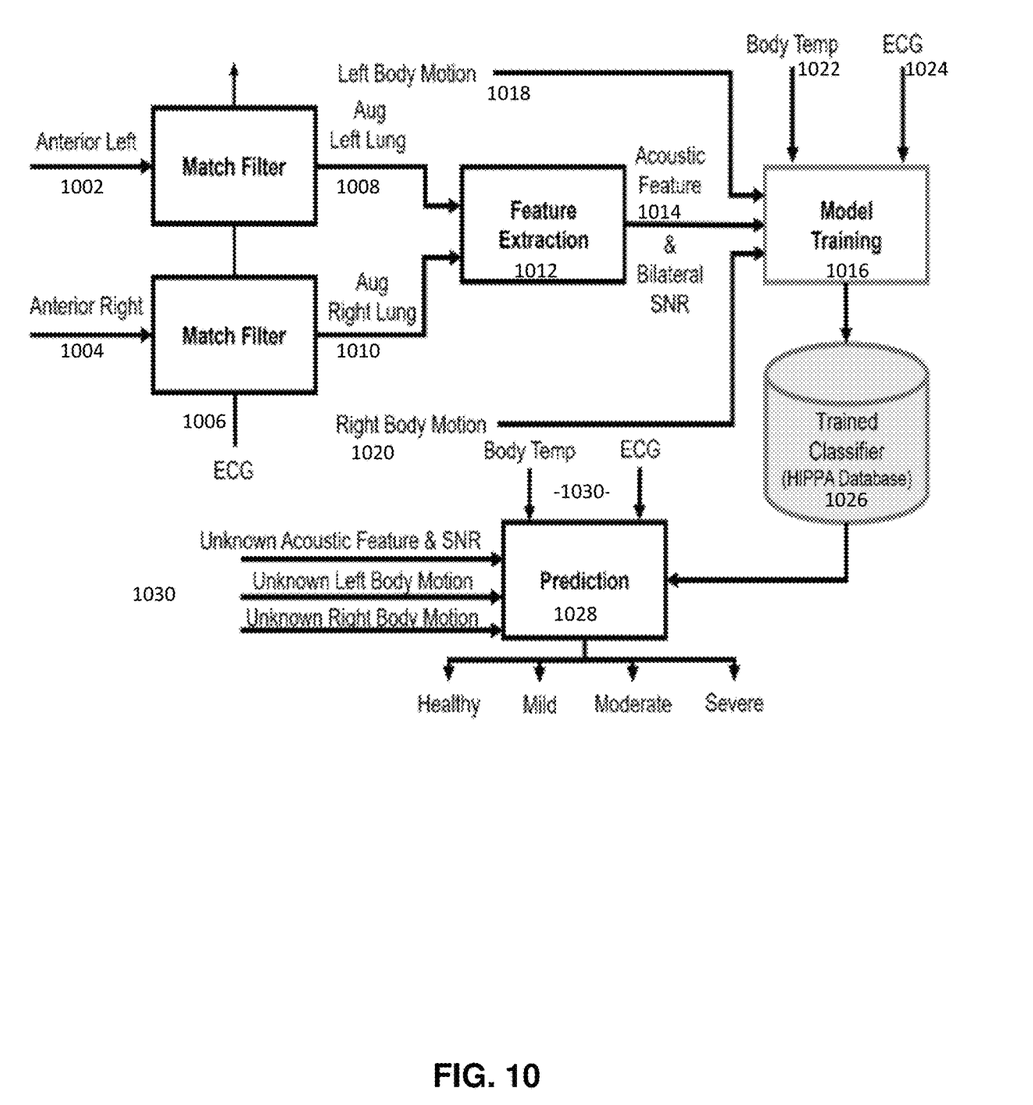
FIG. 10 shows the methodology for bilateral waveform processing and machine learning process for assessing the severity of COPD symptoms.

Overall processing is illustrated in FIG. 10 according to an embodiment. Here the breathing anomaly detection logic takes in bilateral waveforms (1002, 1004) instead of just one. Data 1006 from the ECG sensors is used to Filter out heart noise to only focus on lung sounds. The augmented bilateral lung sounds (1008, 1010) are input to a feature extraction process. The extracted acoustic feature(s) 1014 with bilateral SNR information are passed to a model training process 1016, in addition to left and right body motion information (1018, 1020), temperature information 1022 and ECG datasets 1024. This provides additional information on the subject's motion, body/ambient temperature, and ECG respiration rate to better track the activities that lead to adventitious breathing events. Providing the motion data will also allow training of the classifier 1026 against unwanted background noise have been shown to affect classifier performances. Once trained, the classifier sets can be used by prediction logic 1028 produce four possible prediction values: healthy, mild, moderate, and severe, when presented with input data 1030 from the user's sensors (e.g., motion, acoustic, temperature, and ECG data).

The predicted values can be further mapped to standardized spirometric lung function tests (PFT), such as the forced expiratory volume in one second (FEV1) 1145 or forced vital capacity (FVC) scores. See FIG. 11. The bilateral SNR values are designed to correlate to the gold standard FEV1 scores 1146, through the machine learning process. In an embodiment, the model training logic 1016 and classifier 1026 may be located in an offline server and the remaining logic may be located on a user's mobile device.

Figure 11:
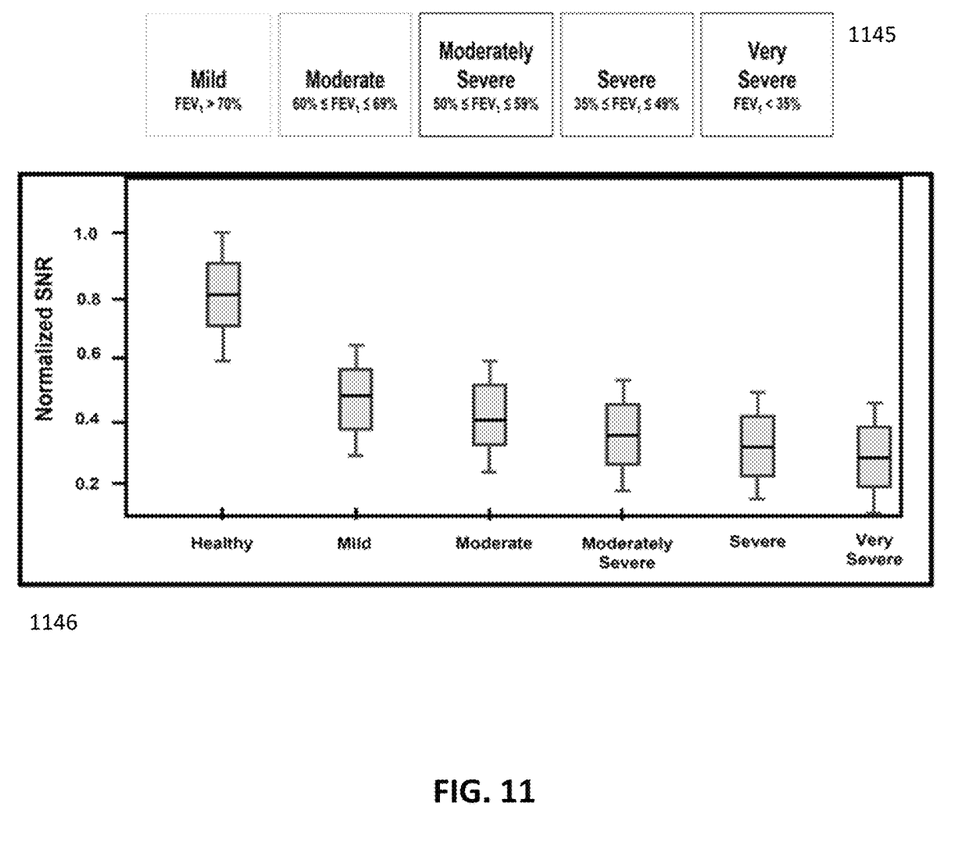
FIG. 11 shows the methodology for measuring respiratory period through a machine learning and artificial intelligence process.

The feature extraction routine can also produce the SNR values for the bilateral case (through array gain processing) that can be used to correlate the intensity/severity of the subject's breathing. This approach can also enable monitoring of specific activities of daily living that induce exacerbation on certain individuals. The bilateral SNR values may be correlated with the output of pulmonary function scores to study the deviation.

Figure 12:
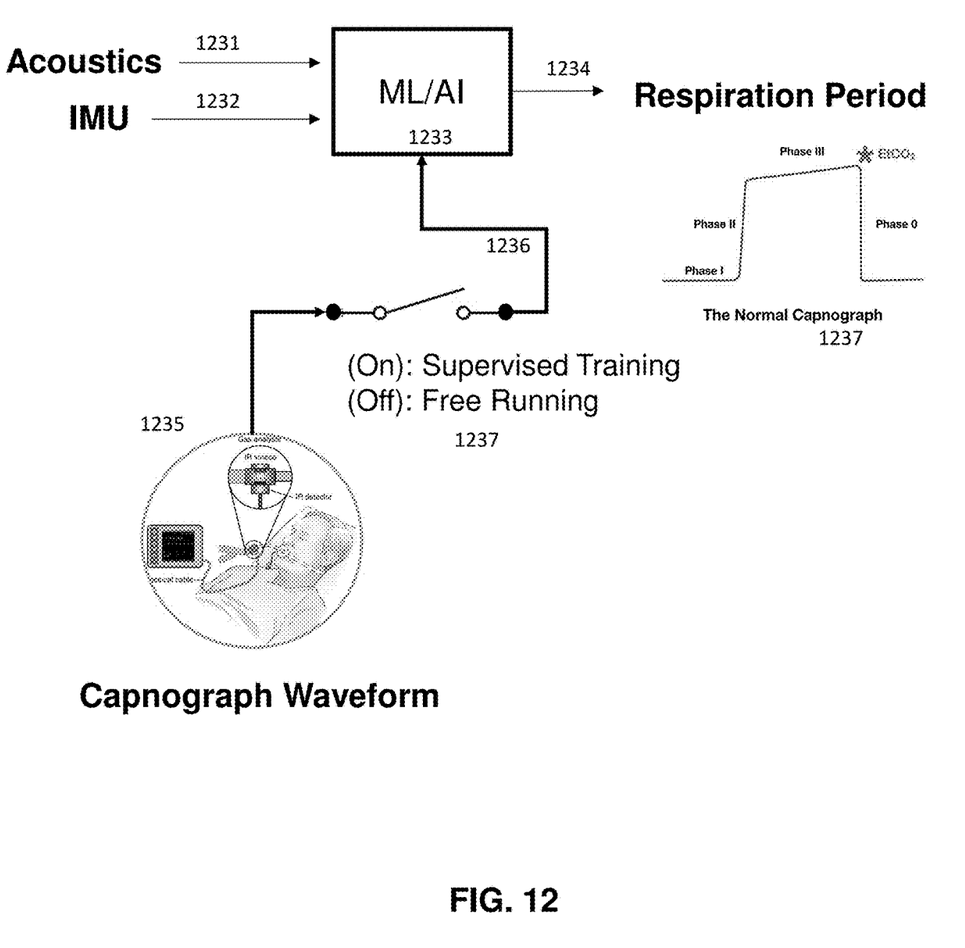
FIG. 12 shows the provider and patient dashboard for visualizing the real-time and recorded data measurements.

In an embodiment, shown in FIG. 12, the device performs respiratory period waveform construction (having output 1234) by combining both the acoustics 1231 and patient motion data 1232 as inputs to another machine learning and artificial intelligence routine (ML/AI) 1233. The output 1234 is the respiratory cycle that mimics the intended signal from a normal capnograph. The rising transition in output 1234 represents an expiratory period; the falling transition in output 1234 represents an inspiratory period. Both should correlate to a normal capnograph 1237. The ML-AI routine 1233 is trained with a capnograph waveform 1235 during supervised learning (where this training input is shown as input 1236) or is allowed to operate in free running mode during normal operation 1237. The output of this embodiment can be used for equivalent $CO_2$ monitoring of patients.

Figure 13:
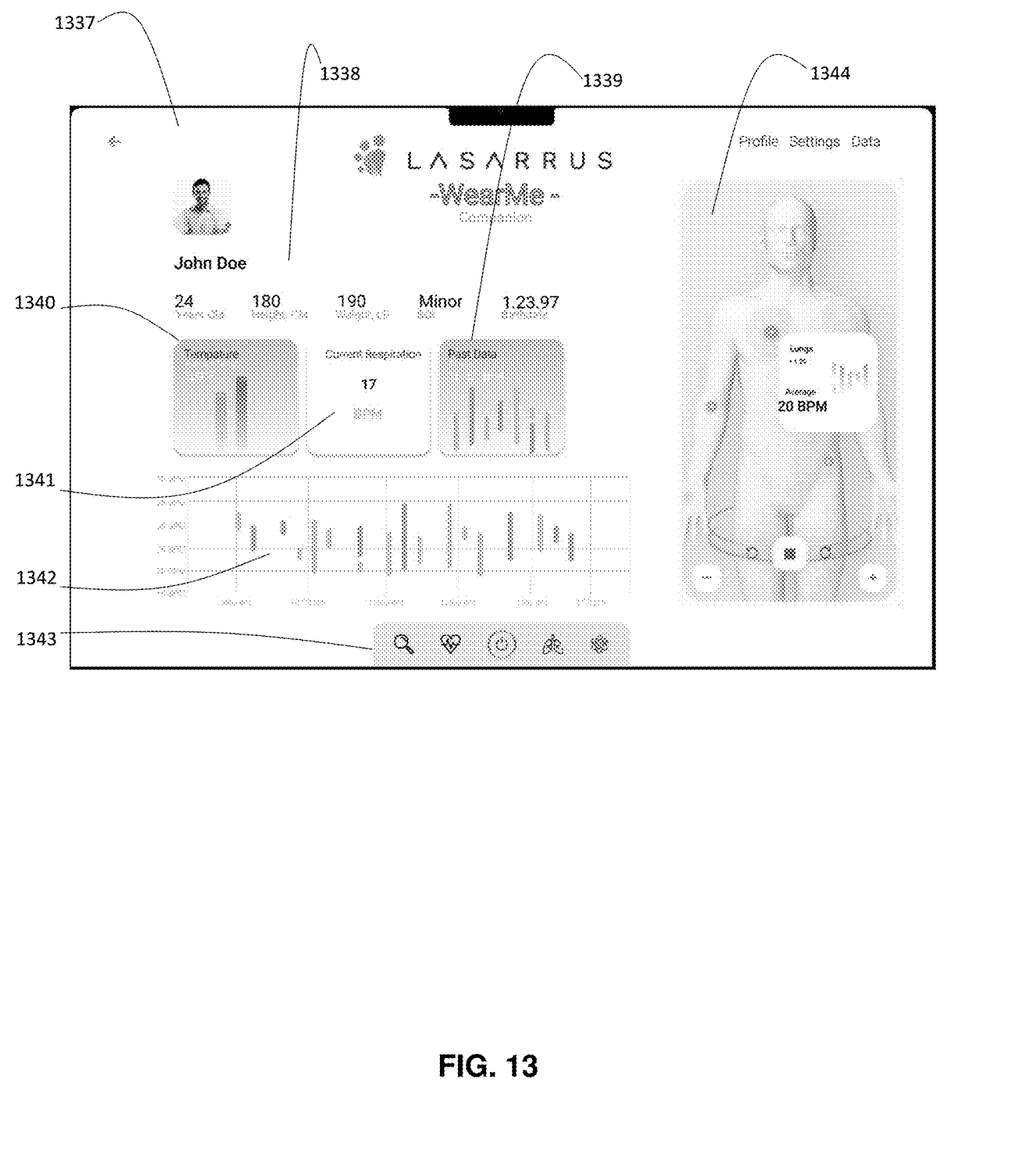
FIG. 13 illustrates a patient-provider dashboard, according to an embodiment.

In an embodiment the data collected by the sensor system is displayed using the patient-provider dashboard (see FIG. 13) showing the user lung information 1337, which allows for collection and display of user meta-data (age, height severity of illness, etc.) 1338. The dashboard can display real-time temperature 1340, respiration rate 1341, respiratory period waveform 1342, and past data 1339. The user can navigate to other menu on the dashboard (e.g., heart and kinematics) 1343. The dashboard may also include a customizable intelligent user avatar 1344 that acts as both a personal wearable assistant and a data interpreter; this allows for improved patient experience, acceptability, and adherence. The illustrated embodiment show's avatar 1344 and a corresponding breath rate (BPM). Alternative embodiments of an avatar may show sensor placement and/or other aspects of lung function such as forced expiratory volume FEV1. The dashboard can be deployed on any platform, smartphone, PC, and on the internet.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

What is claimed is:

1. A system for predicting onset and severity of Chronic Obstructive Pulmonary Disease (COPD) symptoms in a user comprising:

an apparatus wearable by the user having a housing with an exterior surface and an interior cavity, the apparatus including:
a battery disposed in the interior cavity and configured to provide electrical power;

a universal serial bus connection port;
one or more lights in electrical connection with the battery, wherein at least one of the one or more lights are visible from the exterior surface;
a power actuation switch accessible from the exterior surface, the power actuation switch in electrical connection with the battery;
a radio in electrical connection with the battery wherein the radio is configured to transmit sensor data over a wireless communications channel; and
sensors configured to generate the sensor data, the sensors including:
    a digital microphone array in electrical connection with the battery,
    a digital stethoscope in electrical connection with the battery,
    an electrocardiogram sensor in electrical connection with the battery,
    a thermometer in electrical connection with the battery, and
    a goniometer in electrical connection with the battery,
wherein the sensor data comprises electrocardiogram data, user motion data, and user temperature data; and
a server configured to:
    receive the sensor data;
    apply a match filter to data from the user's left lung and right lung;
    extract features from data from the user's left and right lungs to form feature data;
    augment the feature data with additional data to form augmented data, the additional data comprising user motion data, and user temperature data;
    generate a machine learning model, and
    train the machine learning model using the augmented data;
    wherein the machine learning model is configured to make a prediction on the
    onset and severity of COPD symptoms in the user based on incoming sensor data.

2. The system of claim 1, wherein the housing comprises connection points for one or more straps.

3. The system of claim 1, further comprising a mobile device configured to receive the sensor data over the wireless communications channel and to forward the sensor data to the server over a second wireless communications channel.

4. The system of claim 1, wherein the server is further configured to transmit the prediction to a medical provider.

5. The system of claim 1, wherein the server is further configured to generate a questionnaire comprising one or more questions, automatically answer at least one of the questions based on the received sensor data, display the questionnaire to the user, the receive answers to at least one of the one or more questions from the user.

6. The system of claim 3, wherein the mobile device further comprises a user interface configured to generate a digital avatar.

* * * * *